US006476118B1

(12) United States Patent
Karger et al.

(10) Patent No.: US 6,476,118 B1
(45) Date of Patent: Nov. 5, 2002

(54) POLYMER MIXTURES FOR HIGH PERFORMANCE/HIGH TEMPERATURE SEPARATION IN CAPILLARY ELECTROPHORESIS, ESPECIALLY FOR LONG READ DNA SEQUENCING

(75) Inventors: Barry L. Karger, Newton; Lev Kotler, Brighton; Wolfgang Goetzinger; Haihong Zhou, both of Boston; Zoran Sosic, Cambridge, all of MA (US); Oscar Salas-Solano, San Francisco, CA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 09/507,496

(22) Filed: Feb. 18, 2000

Related U.S. Application Data

(60) Provisional application No. 60/132,291, filed on May 3, 1999.

(51) Int. Cl.[7] .............................................. C08L 31/04
(52) U.S. Cl. ........................ 524/521; 204/451; 204/601; 525/218
(58) Field of Search ........................ 524/521; 525/218; 204/601, 451

(56) References Cited

U.S. PATENT DOCUMENTS 6,156,819 A * 12/2000 Lai et al. .................... 523/130

OTHER PUBLICATIONS

CAPLUS Abstract of Baba et al. ("Separation of DNA Fragments by High–Performance Liquid Chromatography and Capillary Electrophoresis", J. Liq. Chromatogr. (1993), 16(4), 945–53).*

Oscar Salas–Solano et al., "Routine DNA Sequencing of 1000 Bases in Less Than One Hour by Capillary Electrophoresis with Replaceable Linear Polyacrylamide Solutions", Analytical Chemistry, vol. 70, No. 19, pp. 3996–4003 (1998).

Eliza N. Fung et al., "High–Speed DNA Sequencing by Using Mixed Poly(ethylene oxide) Solutions in Uncoated Capillary Columns", Analytical Chemistry, vol. 67, No. 13, pp. 1913–1919 (1995).

Annelise E. Barron et al., "The effects of polymer properties on DNA separations by capillary electrophoresis in uncrosslinked polymer solutions", Electrophoresis, vol. 17, pp. 744–757 (1996).

Chunhung Wu et al., "Polyacrylamide solutions for DNA sequencing by capillary electrophoresis: Mesh sizes, separation and dispersion", Electrophoresis, vol. 17, pp. 1103–1109 (1996).

Yongseong Kim et al., "Separation of DNA sequencing fragments up to 1000 bases by using poly(ethlene oxide)–filled capillary electrophoresis", Jounal of Chromatography A, vol. 781, pp. 315–325 (1997).

Yongseong Kim et al., "DNA sequencing with pulsed–field capillary electrophoresis in poly(ethylene oxide) matrix", Electrophoresis, vol. 18, pp. 2901–2908 (1997).

* cited by examiner

*Primary Examiner*—Ana Woodward
(74) *Attorney, Agent, or Firm*—Weingarten, Schurgin, Gagnebin & Lebovici LLP

(57) ABSTRACT

A method of separating a mixture of biopolymers of various lengths using a blend of two linear hydrophilic polymers, particularly polyacrylamides (LPA) or substituted polyacrylamides, one with high weight-average molecular mass and another with low weight-average molecular mass, each present at a low concentration but wherein the concentration of the high weight-average molecular mass LPA is above its entanglement threshold, is disclosed. The matrix is excellent for use in methods of nucleic acid analysis, particularly long read length DNA sequencing.

4 Claims, 3 Drawing Sheets

POLYMER MIXTURES FOR HIGH PERFORMANCE/HIGH TEMPERATURE SEPARATION IN CAPILLARY ELECTROPHORESIS, ESPECIALLY FOR LONG READ DNA SEQUENCING

CROSS REFERENCE TO RELATED APPLICATIONS

This application claims the priority of U.S. Provisional Patent Application No. 60/132,291 filed, May 3, 1999 entitled POLYMER MIXTURES FOR HIGH PERFORMANCE/HIGH TEMPERATURE SEPARATION IN CAPILLARY ELECTROPHORESIS, ESPECIALLY FOR LONG READ DNA SEQUENCING, the whole of which is hereby incorporated by reference herein.

STATEMENT REGARDING FEDERALLY SPONSORED RESEARCH OR DEVELOPMENT

Part of the work leading to this invention was carried out with United States Government support provided under a grant from the Department of Energy, Grant No. DE-FG02-90ER-60985. Therefore, the U.S. Government has certain rights in this invention.

BACKGROUND OF THE INVENTION

Capillary array electrophoresis is the method of choice for fast reliable DNA sequencing, or other DNA analysis, using automated, commercial sequencing instruments. However, the read length per capillary run that these instruments can deliver is typically no longer than 600–800 bases. To increase the read length further, the separation polymer matrix as well as the separation conditions need to be improved.

It is well known that an elevated column temperature helps to resolve compressions and to increase read length by relaxing stretched DNA in the applied field. An optimum separation of 1000 bases with 97% accuracy has been achieved at 150 V/cm and a column temperature of 50° C. with a matrix containing 2% w/w of a high molecular mass LPA (Carrilho et al., Anal. Chem. 68:3305–3313, 1996). If elevations in column temperature for a sequencing run beyond 50° C. were obtainable, even longer read DNA sequencing lengths should be achievable. However, the thermal stability of the polymer solution network puts limits on the maximum possible column temperature for sequencing runs.

BRIEF SUMMARY OF THE INVENTION

We have determined that a blend of two hydrophilic polymers (e.g., polymers having alkyl residue groups, particularly linear polyacrylamides (LPA) or substituted polyacrylamides), one with high weight-average molecular mass (HMM), 5,000,000 or higher, and another with low weight-average molecular mass (LMM), 200,000 or higher, each present at a low concentration but wherein the concentration of the HMM LPA is above its entanglement threshold, forms an excellent, thermally stable matrix for long read length DNA sequencing. The molecular mass of the low molecular mass polymer is preferably up to about 15% of the mass of the high molecular mass polymer. Polymer separations using the matrix of the invention can be carried out at elevated temperatures, e.g., 70° C., for improved selectivity in the long-base-fragment region.

In a preferred embodiment, the concentration of the low weight-average molecular mass LPA polymer is from 0.25% to 2%, the concentration of the high weight-average molecular mass LPA polymer is from 1.5% to 4% and the ratio of the concentration of the low-weight-average molecular mass LPA polymer to the concentration of the high-weight-average molecular mass LPA polymer is from 1:25 to 1:2.

Preferably, in the method of the invention, the device for conducting capillary electrophoresis is a coated capillary tube or integrated microchannel device. Preferred coatings are, e.g., covalent, adsorbed or polymer matrix adsorbed.

BRIEF DESCRIPTION OF THE THE DRAWINGS

Other features and advantages of the invention will be apparent from the following description of the preferred embodiments thereof and from the claims, taken in conjunction with the accompanying drawings, in which:

FIGS. 1A and 1B show the effect of replacing 50 kDa LPA with 270 kDa LPA in a mixed separation matrix on (A) separation selectivity ($\Delta\mu/\bar{\mu}$) and (B) efficiency at different temperatures. Matrices and temperatures: 2% (w/w) 10 MDa/0.5% (w/w) 50 kDa, 60° C. (▲), 2% (w/w) 10 MDa/0.5% (w/w) 270 kDa, 60° C. (●) and 2% (w/w) 10 MDa/0.5% (w/w) 270 kDa, 70° C. (■)

DETAILED DESCRIPTION OF THE INVENTION

Figure 1:
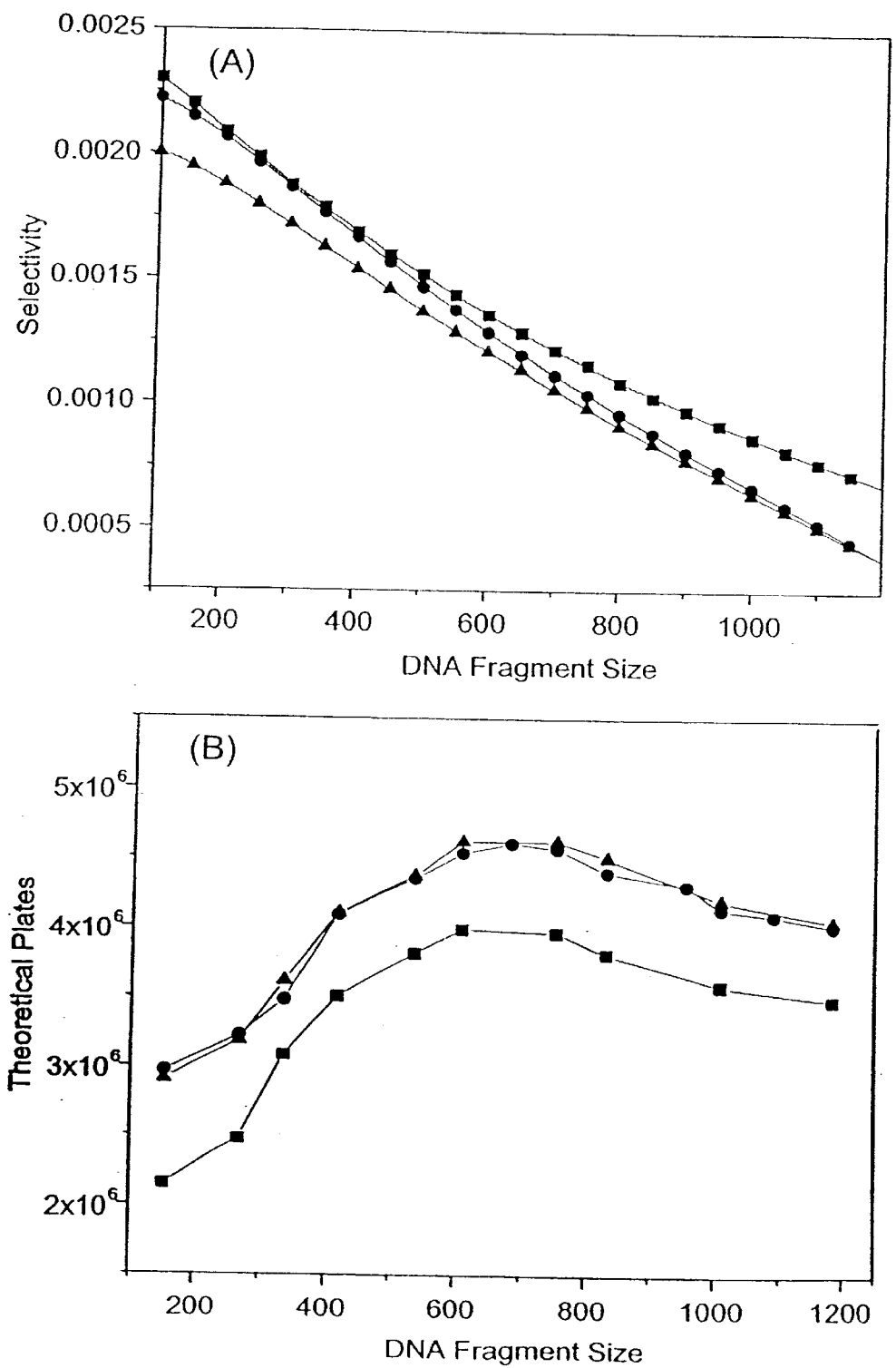

We have recently introduced a mixed matrix containing a blend of high weight-average molecular mass LPA and low weight-average molecular mass LPA. Our first embodiment consisted of 2% HMM LPA (10 MDa) and 0.5% LMM LPA (50 kDa). With this matrix, the optimal column temperature was found to be 60° C., or 10° C. higher than with HMM LPA alone. At the same time, it was possible to increase field strength to 200 V/cm, and the resulting read length of 1000 bases was achieved in less than an hour with a read accuracy of 99%.

We have now discovered that using 0.5% of 270 kDa LPA instead of 50 kDa LPA in the matrix unexpectedly resulted not only in a further increase of column temperature, to 70° C., but also in an increase in selectivity at both low and high fragment size of the separated sample. At this column temperature and at an electric field of 125 V/cm, read length was extended to 1300 bases in roughly 2 hours. These results were particularly unexpected both because the average mesh size is predicted to be the same for 50 kDa LPA and 270 kDa LPA (deGennes, *Scaling Concepts in Polymer Physics*, Cornell University Press: Ithaca, N.Y., 1979) and also because the actual average mass added to the total mass of the matrix by an increase from 50 to 270 kDa in the weight-average molecular mass of the low molecular mass polymer is negligible.

While not being bound by any theory, we note that the most important factor that affects read length in DNA sequencing is electrophoretic resolution, which is a function of selectivity and efficiency of separation (Giddings, Sep. Sci. 4:181–189, 1969; Karger et al., *An Introduction to Separation Science,* J. Wiley & Sons: N.Y., 1973). Separation selectivity is a normalized distance between two peaks and is defined as ($\Delta\mu/\bar{\mu}$), where $\Delta\mu$ is the difference in mobility between two peaks and $\bar{\mu}$ is the mean mobility of the two peaks. Efficiency, given in theoretical plates, is a measure of peak broadening. For long DNA fragments, selectivity has a small absolute value, and resolution of such fragments demands efficiencies of millions of theoretical plates, which can be obtained with capillary columns filled with replaceable polymer solutions.

Efficiency is related to the total variance of peak width, which results from several linearly independent variances (Mullikin et al., Science 283:1867–1868, 1999): the variance due to molecular diffusion, the variance due to the matrix network dynamic dissociation and polymer-DNA interactions, the variance due to temperature profile across the column, the variance due to electroosmotic flow, and the variance due to extracolumn effects related to injection and detection. Other band broadening factors exist but are in general less important.

While molecular diffusion is effectively suppressed in entangled polymer solutions relative to free solution, it necessarily becomes larger with increasing temperature (Slater, Electrophoresis 14:1–7.4, 1993). Variance due to electroosmotic flow can be effectively limited by covalent, dynamic or adsorptive coating of the capillary walls to minimize the zeta potential at the walls, and the thermal gradient across the capillary column is negligible with effective column temperature control and use of a low conductivity running buffer. Band broadening due to the finite length of the detection window can be decreased by tightly focusing the laser to illuminate a very small region. The width of the injection plug can be minimized by optimizing injection conditions, such as field amplification sample focusing, electric field strength, and duration, and the size and composition of the sample aliquot (Salas-Solano et al., Anal. Chem. 70:1528–1535.5, 1998).

Band broadening related to polymer-DNA interactions and to polymer network dynamics can be controlled through polymer type, molecular size and concentration. For example, polymer-DNA hydrophobic interactions are minimized using very hydrophilic polymers such as polyacrylamide. The hydrophobicity of DNA increases with base number; hence hydrophobic polymers are less suitable for long read DNA sequencing. Network dynamics, reflected in the rate of dissociation of entanglements (constraint release (Duke et al., Phys. Rev. E 49:2408–2416.6, 1994) and in the lifetime of pores within the entangled strands, can be expressed through the network relaxation time. This parameter is inversely proportional to the column temperature (e.g., pore lifetime diminishes with temperature increase) and directly proportional to the cubic weight average molecular mass of the polymer (Cottet et al., Electrophoresis 19:2151–2162, 1998). Relaxation time also increases, but more slowly, with an increase in polymer concentration. Among other factors, a decrease in pore lifetime can lower efficiency by leading to enhanced molecular diffusion. In addition, selectivity can be affected, since pore lifetime should be greater than the residence time of the DNA molecule segment in the pore (Cottet et al., Electrophoresis 19:2151–2162, 1998; Bae et al., J. Chromatogr. A 652:17–22.7,8, 1993) in order to maintain a uniform migrational behavior (i.e., mobility) for DNA fragment molecules throughout the polymer solution matrix. Concentrated polymer solutions, however, are not optimal for separation of long DNA fragments, and therefore, the use of solutions of a high molecular mass polymer at relatively dilute concentrations is important for obtaining long read lengths.

In addition to the relationship of pore lifetime to solute residence time, selectivity is obviously dependent on DNA migration processes. According to the latest version of the biased reptation model of DNA migration (Duke et al., Phys. Rev. E 49:2408–2416, 1994; Semenov et al., Phys. Rev. E 51:1520–1537, 1995), the size threshold beyond which DNA molecules become fully oriented in the direction of the electric field, with all DNA migrating at the same rate, increases with decreasing electric field strength and with increasing column temperature. Therefore, by increasing the column temperature and decreasing the electric field, longer read lengths can be obtained.

The following examples are presented to illustrate the advantages of the present invention and to assist one of ordinary skill in making and using the same. These examples are not intended in any way otherwise to limit the scope of the disclosure.

Thermostabilization of entanglements in the separation matrix by LMM LPA. An elevated column temperature, if achievable, will be beneficial for long reads (higher resolution, fewer compressions, faster separation). Faster separation speed and a reduction in compressions at elevated temperature also have been noted by others (see, e.g., Zhang et al., Anal. Chem. 67:4589–4593, 1995). However, while raising the temperature increases the threshold DNA size at which oriented reptation dominates, each matrix must have some optimum temperature above which the combined effects of greater thermal diffusion and shortened relaxation time of the polymer network diminish the separation of large DNA fragments. Polymer matrices with more stabilized entanglements provide optimum separation at higher temperature than others and are more thermally stable.

We have shown that the addition of 0.5% (w/w) 50 kDa LPA substantially increases the thermostability of the network in a 2% (w/w) 10 MDa LPA matrix without significant increasing viscosity and thereby migration time (Salas-Solano et al., Anal. Chem. 70:3996–4003, 1998). For this mixed matrix, an optimum temperature of 60° C. for a one-hour separation was found, 10° C. higher than for a matrix containing 2% (w/w) HMM LPA alone. To examine the stabilizing effect in more detail, selectivity and efficiency were plotted as a function of DNA size using different mixed matrices and run temperatures. In the first experiments, 50 kDa LPA was replaced by 270 kDa LPA. Samples were prepared using Universal BigDye-labeled (−21) primer cycle sequencing with AmpliTaq-FS on ssM13mp18 template, as described in Materials and Methods. An additional G-terminated reaction was added for better resolution. Electrophoretic conditions were 75 $\mu$m i.d., 365 $\mu$m o.d., poly(vinyl alcohol)-coated capillary with effective length 30 cm, total length 45 cm; both running buffers were 50 mM Tris/50 mM TAPS/2 mM EDTA. The cathode running buffer and separation matrix also contained 7 M urea. Samples were injected at a constant electric field of 9 V/cm (I=0.7 $\mu$A) for 10 s and electrophoresed at 125 V/cm. As can be seen in FIGS. 1A and 1B, substituting 270 kDa LPA for 50 kDa LPA at 60° C. yielded an unexpected increase in selectivity at the beginning of the electropherogram, although the difference in selectivity relative to the 50 kDa LPA diminished as the DNA size increased. By comparison, when 270 kDa LPA was used at 70° C., greater selectivity was maintained throughout the run. Efficiency was identical for both mixed matrices in the 60° C. runs but decreased slightly when the temperature was raised to 70° C. The enhanced selectivity at large fragment sizes permitted greater read lengths, confirming that thermostabilization is a main feature of LMM LPA. Experiments carried out with 500 kDa LPA at 0.25% (w/w) and 0.5% (w/w) do not appear to show any significant improvement in read length beyond that provided by 270 kDa LPA. However, the results are still better than those obtained with 50 kDa LPA.

Figure 2:
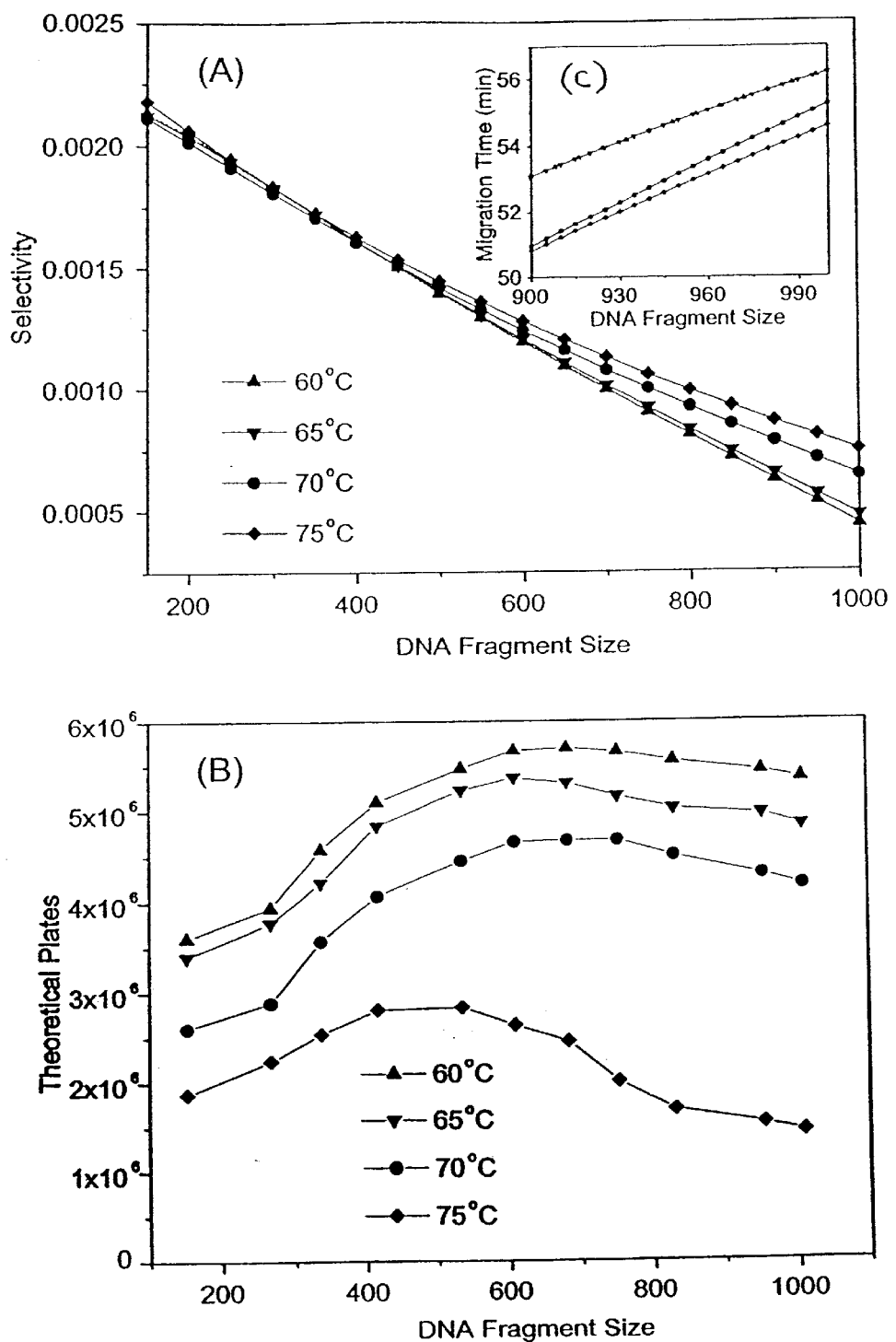
FIGS. 2A and 2B show the effects of optimizing the column temperature for a mixed LPA matrix of 2% (w/w) 10 Mda and 0.5% (w/w) 270 kDa LPA on (A) separation selectivity ($\Delta\mu/\bar{\mu}$) and (B) efficiency for single-stranded DNA sequencing fragments at 60° C. (▲), 65° C. (▼), 70C (●) and 75° C. (♦)
FIG. 2C shows the effect of temperature on migration time for the experiments shown in FIGS. 2A and 2B.

FIGS. 2A and 2B show the effect of varying column temperature on separation selectivity (2A) and efficiency (2B), respectively, for a matrix of 2% (w/w) 10 Mda and 0.5% (w/w) 270 kDa LPA. Sequencing products, prepared with BigDye-labeled primers and M13mp18 template, were run at 200 V/cm. For DNA fragments longer than about 500 bases, selectivity increased significantly above 65° C. as seen by the changes in slope in FIG. 2A. As shown in FIG. 2B, efficiency was greatest at the lowest temperature (60° C.) as expected, but did not decrease drastically until 75° C. The greatest overall resolution occurred at 70° C., where the added selectivity more than compensated for the loss in efficiency. As shown in FIG. 2C, raising the temperature to 70° C. reduced migration time as well. The greater stability achieved by increasing the molecular mass of the LMM component from 50 kDa to 270 kDa is surprising given the expectation that there would be no change in mesh size for this small a percentage change in total molecular mass.

Electric Field Optimization. The read length obtained at 200 V/cm and 70° C. with the mixed matrix containing 2% (w/w) 10 MDa and 0.5% 270 kDa LPA, without optimizing the run conditions, was ~1000 bases with 99% accuracy, the same result as obtained under optimum conditions with 50 kDa LPA. However, using the new mixed matrix, it was possible to improve read length further by decreasing the electric field and thereby reducing the field-parallel orientation of the long DNA fragments. The results of field optimization at a constant temperature of 70° C. are shown in Table 1.

TABLE 1

Effect of Electric Field Strength on DNA Sequencing Results with LPA 2% (w/w) 10 MDa/0.5% (w/w) 270 kDa at 70° C.[a]

| Electric Field (V/cm) | Migration Time for Base 1019 (min) | Fragment Size at Resolution 0.3 | Read Length[b] at 98.5% Accuracy |
|---|---|---|---|
| 250 | 44.0 | 871 | 927 |
| 200 | 55.6 | 995 | 1042 |
| 150 | 80.5 | 1060 | 1127 |
| 125 | 101.0 | 1168 | 1190 |
| 100 | 131.0 | 1236 | 1172 |

[a]Samples and other electrophoretic conditions were as in FIG 1. Values in the table are averages of 3 to 5 experiments.
[b]For a specified accuracy, read length was defined as the longest stretch of called sequence having that overall accuracy.

This table shows that lowering the field from 250 V/cm to 100 V/cm indeed increased the DNA size at which a resolution of 0.3 (an arbitrarily chosen low value, which permitted focusing on the separation of long DNA fragments) was achieved, from 871 to 1236 bases. The greatest benefit occurred below 150 V/cm; the increment of 108 bases between 150 to 125 V/cm was 60% higher than the 65-base difference between 200 to 150 V/cm, despite the smaller field change.

Lowering the field from 150 to 125 V/cm experimentally increased read length less than it did the fragment size at resolution 0.3, and a further field decrease to 100 V/cm even reduced read length slightly, despite the higher selectivity and higher resolution in the region of high base numbers. The major parameter counteracting higher resolution appeared to be the decline in signal intensity with decreasing field. As expected, the time required for separation, shown in Table 1 by the migration time for a fragment of 1019 bases, increased as the field was lowered.

Effect of Mixture Composition on Sequencing. To test whether an even longer LPA might further improve read length, HMM LPA was synthesized with a molecular mass of 17 MDa. Table 2 summarizes results from different LPA mixtures employing this and other polymer preparations under comparable conditions of polymer concentration, temperature and field.

TABLE 2

Effect of Polymer Composition on DNA Sequencing Results[a]

| LPA | Temperature (° C.) | Electric Field (V/cm) | Migration Time for Base 1019 (min) | Fragment Size at Resolution 0.3 | Read Length[b] at 98.5% Accuracy |
|---|---|---|---|---|---|
| 2% 17 MDa + 0.5% 270 kDa | 70 | 125 | 105.4 | 1222 | 1257 |
| 2% 10 MDa + 0.5% 270 kDa | 70 | 125 | 101.0 | 1168 | 1190 |
| 2% 17 MDa + 0.5% 50 kDa | 70 | 125 | 100.0 | 1060 | 1083 |
| 2% 10 MDa + 0.5% 500 kDa | 70 | 125 | 99.5 | 923 | 965 |
| 2% 10 MDa + 0.5% 50 kDa[c] | 60 | 200 | 55.6 | 927 | 1013 |
| 2% 10 MDa[d] | 50 | 150 | 81.0 | 925 | 951 |

[a]Samples and other electrophoretic conditions were as described herein. Values are averages of 3 to 5 experiments. Temperature and electric field were optimized for each polymer matrix.
[b]For a specified accuracy, read length was defined as the longest stretch of called sequence having that overall accuracy.
[c]Conditions same as optimum conditions determined in Salas-Solano et al., Anal. Chem. 1998, 70, 3996–4003.
[d]Conditions same as in Goetzinger et al., Electrophoresis 1998, 19, 242–248.

As can be seen in Table 2, increasing the molecular mass of either the LMM or HMM component increased both resolution and read length. Read length was strongly correlated with the fragment size at which a resolution of 0.3 was achieved, indicating that improved resolution was the source of greater read length under these conditions of temperature and field. It should be emphasized that increasing molecular mass of either LPA component had negligible effect on migration time.

Figure 3:
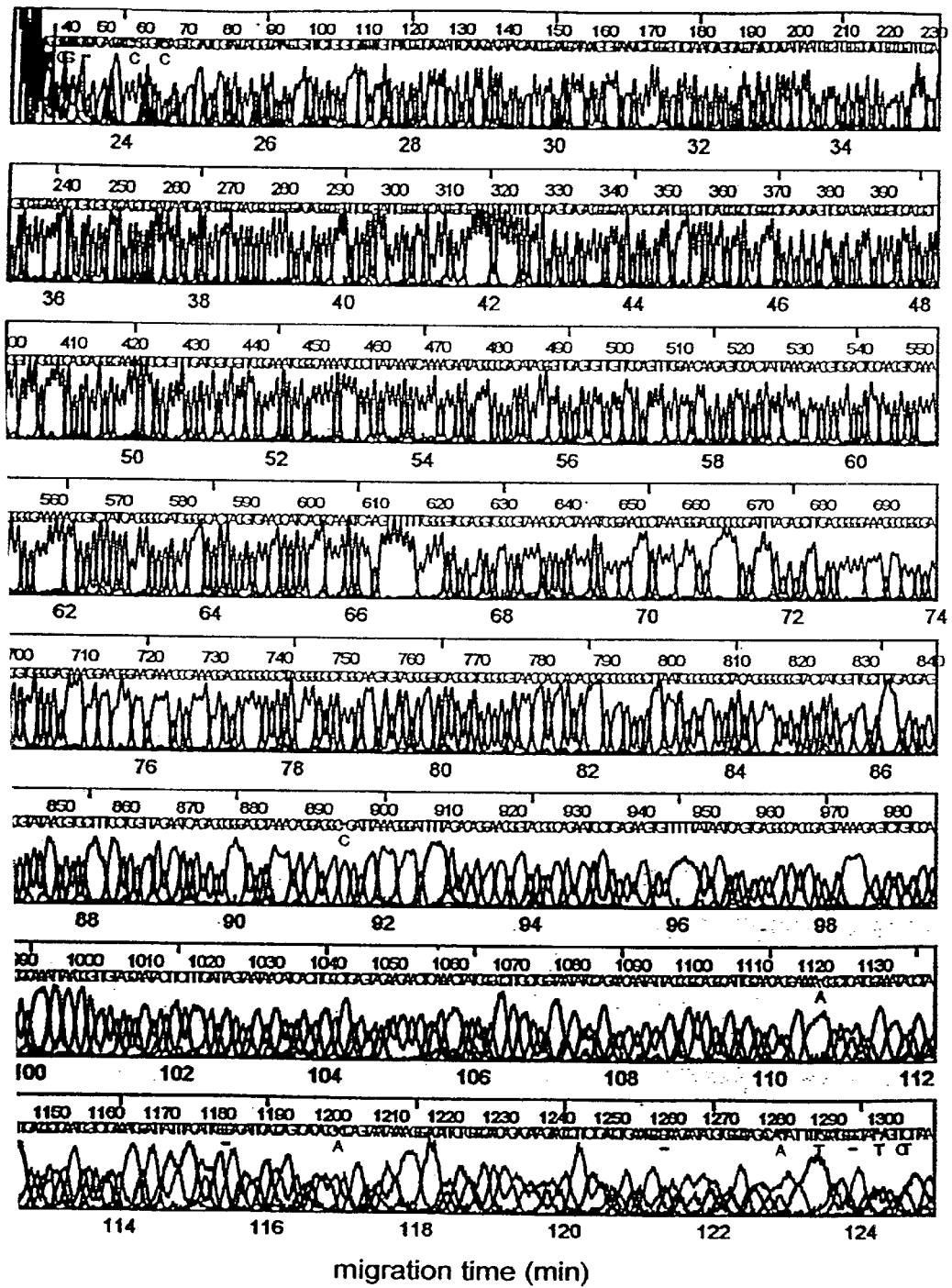
FIG. 3 is an electropherogram showing that a read length of 1300 bases was obtained using the separation matrix LPA 2.0% (w/w) 17 MDa/0.5% (w/w) 270 kDa at 125 V/cm and 70° C.

The longest read length, an average ~1260 bases with 98.5% accuracy, was found by combining the largest LMM LPA (270 kDa) with the largest HMM LPA (17 MDa). FIG. 3 is an electropherogram generated with this matrix that shows a read length of 1300 bases with 98.5% accuracy. A few miscalls at the beginning were followed by over 800 correctly called bases, and errors did not begin to accumulate until base 1240. The cause of base-calling inaccuracy beyond this point was low resolution, whereas at field strengths lower than 125 V/cm, problems occurred earlier in the sequence due to low signal. For the runs summarized in Tables 1 and 2, read lengths for 99% accuracy were approximately 30–60 bases less than given for 98.5% accuracy.

The sequencing results obtained with the mixed matrix of the invention can also be improved by optimizing base-caller accuracy. Table 3 shows the read lengths obtained on a set of M13 runs performed under the new conditions of 70°

C. and 125 V/cm using different versions of the base-caller software for long-read sequencing described in Materials and Methods.

TABLE 3

Progress in Software for Long Read Lengths[a]

|  | Limiting Resolution | Read Length[b] | |
|---|---|---|---|
|  |  | 99% Accuracy | 98% Accuracy |
| Graph-theoretic base-caller[c] | 0.40 | 890 | 960 |
| First version of expert system[d] | 0.25 | 1060 | 1210 |
| Current version of expert system | 0.25 | 1200 | 1290 |

[a]Results of different base-caller versions on a set of five M13 electropherograms run at 125 V/cm and 70° C. for about 2 hours.
[b]For a specified accuracy, read length was defined as the longest stretch of called sequence having that overall accuracy.
[c]From Carrilho et. al., Anal. Chem. 1996, 68, 3305–3313.
[d]From Salag-Solano et al., Anal. Chem. 1998, 70, 3996–4003.

A precondition for obtaining the longest read length from a given sequencing electropherogram is accurate base-calls at low resolution. The effect of reducing the limiting resolution of the base-caller from 0.40 to 0.25 is reflected in the ~200 bases added between the graph-theoretic base-caller employed in 1996 and the first version of the expert system developed in 1998. Resolution is not the only parameter affecting base-caller accuracy, however, and while the original expert system was accurate to a resolution of 0.25 on data obtained at 200 V/cm, it was not as good on the new 125 V/cm data summarized in Table 3. Lowering field strength from 200 to 125 V/cm commonly resulted in a two- to three-fold smaller signal-to-noise ratio at fixed resolution.

To improve accuracy at 125 V/cm, the number of times that the rules were cycled through to refine base-call assignments was increased, and rules relating to noise level were added. At 125 V/cm, the improvement in read length, compared to a previous version of the base-caller, was 90 bases at 98% accuracy and 140 bases at 99%. Changes to the base-caller were always validated on human genomic templates to ensure that they improved performance on data that would be observed in production sequencing.

Under optimum conditions, the combined effects of mixing 0.5% (w/w) 270 kDa and 2% (w/w) 17 MDa LPA produced a dramatic increase in read length over 2% (w/w) 10 MDa LPA alone. The 17 MDa polymer may create a more rigid network with superior strength of entanglements at high temperature, since the relaxation time of the network depends strongly on polymer molecular mass. However, the additional stabilization of entanglements in the LPA network by the 270 kDa LPA, especially at high temperature, was also clearly important.

While M13 is a model template, its use does indicate the potential results with production templates. For example, samples prepared from cloned fragments of human genomic DNA, primarily from chromosome 17, were sequenced using the mixed matrix of 2% (w/w) 17 MDa and 0.5% (w/w) 270 kDa LPA under run conditions optimized using M13 template. Read lengths up to 1220 bases at 98.5% accuracy were obtained. These templates were prepared for commercial sequencers, which have been optimized for shorter sequences. Therefore, the average read length of ~1100 bases was less than that observed for M13, primarily because of the low signal obtained. Improving the signal could produce read lengths approaching those achieved with M13.

Materials and Methods

Polymerization of Acrylamide. Linear polyacrylamides (LPA) with different molecular masses were prepared in-house in powder form using high purity polymers. High weight-average molecular mass (HMM) LPA was made by inverse emulsion polymerization (Goetzinger et al., Electrophoresis 19:242–248, 1998). Low weight-average molecular mass (LMM) LPA was produced by polymerization of acrylamide in methanol at 60° C. for 4 h using 2,2'-azobisisobutyronitrile as the initiator. After polymerization was complete, the LPA powder was washed with acetone and vacuum-dried. Mixed LPA solutions were prepared as described previously (Salas-Solano et al., Anal. Chem. 70:3996–4003, 1998).

Characterization of Linear Polyacrylamide. Multi-angle laser light scattering (MALLS) is one of the few absolute methods that can be employed to determine the weight-average molecular mass, $M_w$, and coil radius (radius of gyration) of HMM polymers in dilute solution and was used to measure $M_w$ for the LPAs described herein, with tandem GPC-MALLS being utilized to provide size distributions for LMM LPAs. GPC was not employed for HMM LPAs because of lack of separation at 10 MDa and above and the absence of LPA size standards above 9 MDa. (See, e.g., Zimm, J. Chem. Phys., 13:141–145, 1945; Wyatt, Anal. Chim. Acta 272:1–40, 1993).

Sequencing Chemistries. DNA sequencing reactions were prepared using cycle sequencing chemistry with AmpliTaq-FS BigDye (−21) M13 universal primers (PE Biosystems, Foster City, Calif.) with ssM13mp18 (New England Biolabs, Beverly, Mass.) and with M13 clones from human chromosome 17 (Whitehead Institute/MIT Center for Genome Research) as templates. The temperature-cycling protocol was similar to that described previously (Salas-Solano et al., Anal. Chem. 70:3996–4003, 1998).

Software. Data processing was accomplished by an updated version of a known base-calling expert system as described in co-pending U.S. application Ser. No. 09/291,679, hereby incorporated by reference herein.

Other Embodiments

High weight average molecular mass (HMM) linear polyacrylamide above a weight average molecular mass of 5 MDa can be used in mixed matrixes for long read DNA sequencing. The invention has been described above in a particularly preferred embodiment of a mixed LPA matrix of 2% (w/w) 17 Mda and 0.5% (w/w) 270 kDa LPA. If the molecular mass of the HMM LPA is in the range from 5 to 10 MDa, its concentration in the separation matrix may have to be increased up to 4% w/w. Although, in general, a higher concentration of high molecular mass LPA in the separation matrix is not preferable for long read sequencing, this measure will help to increase the thermostability and ensure the entanglement of the matrix. On other hand, if LPA having a weight-average molecular mass substantially higher than 17 MDa is available, its concentration in the mixed separation matrix may be decreased from 2% w/w to 1.5–1.8% w/w. These very high weight-average molecular mass LPAs should have a higher thermostability and a lower entanglement threshold concentration than their 5 to 10 MDa counterparts. The low weight average molecular mass component of the separation mixed matrix may have to be adjusted in conjunction with these changes. In matrices with a higher concentration of the high weight-average molecular mass LPA, a smaller amount of low weight-average molecular mass polymer can be used. More diluted solutions of high weight average molecular mass LPA may be mixed with higher quantities of a low molecular mass component, thus changing the ratio of these LPAs in the mixture from 1:2 to 1:25.

Applications other than long read DNA sequencing may also require different separation matrix formulations. For example, in rapid sequencing of short single-stranded DNA fragments or PCR products at high column temperatures, the concentration of each polymer component in the matrix may be increased, in order to gain selectivity and to compensate for efficiency drop in the region of small fragment sizes. For double-stranded DNA fragment analysis applications, a higher concentration of the low molecular mass component may be required.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A separation matrix for nucleic acid analysis comprising a mixed linear hydrophilic polymer matrix solution, said solution comprising at least one high weight-average molecular mass hydrophilic polymer and at least one low weight-average molecular mass hydrophilic polymer, wherein said high weight-average molecular mass hydrophilic polymer has a molecular mass of 5,000,000 daltons or higher, said low weight-average molecular mass hydrophilic polymer has a molecular mass of 200,000 daltons or higher and, furthermore, the molecular mass of said low weight-average molecular mass hydrophilic polymer is less than or equal to 15% of the molecular mass of said high weight-average molecular mass hydrophilic polymer, and wherein, further, the concentration of said high weight-average molecular mass is above its entanglement threshold.

2. A separation matrix for nucleic acid analysis comprising a mixed linear polyacrylamide (LPA) polymer matrix solution, said solution comprising at least one high weight-average molecular mass LPA polymer and at least one low weight-average molecular mass LPA polymer, wherein said high weight-average molecular mass LPA polymer has a molecular mass of 5,000,000 daltons or higher, said low weight-average molecular mass LPA polymer has a molecular mass of 200,000 daltons or higher and, furthermore, the molecular mass of said low weight-average molecular mass LPA polymer is less than or equal to 15% of the molecular mass of said high weight-average molecular mass LPA polymer, and wherein, further, the concentration of said high weight-average molecular mass LPA is above its entanglement threshold.

3. A separation matrix for nucleic acid analysis comprising a mixed linear polyacrylamide (LPA) polymer matrix solution, said solution comprising about 2.0% (w/w) 17 megadaltons (MDa) LPA and about 0.5% (w/w) 270 kilodaltons (KDa) LPA.

4. A separation matrix for nucleic acid analysis comprising a mixed linear polyacrylamide (LPA) polymer matrix solution, said solution comprising about 2.0% (w/w) 10 megadaltons (MDa) LPA and about 0.5% (w/w) 270 kilodaltons (KDa) LPA.

* * * * *

UNITED STATES PATENT AND TRADEMARK OFFICE
CERTIFICATE OF CORRECTION

PATENT NO. : 6,476,118 B1
DATED : November 5, 2002
INVENTOR(S) : Barry L. Karger et al.

It is certified that error appears in the above-identified patent and that said Letters Patent is hereby corrected as shown below:

Column 2,
Line 29, "70C" should read -- 70°C --;

Column 6,
Table 2, line 30, "500 kDa" should read -- 50 kDa --; and

Column 7,
Line 21, "Salag-Solano" should read -- Salas-Solano --.

Signed and Sealed this

Twelfth Day of August, 2003

JAMES E. ROGAN
*Director of the United States Patent and Trademark Office*